(12) United States Patent
Kusaki et al.

(10) Patent No.: US 9,034,661 B2
(45) Date of Patent: May 19, 2015

(54) METHOD FOR PRODUCING MOLECULE IMMOBILIZING SUBSTRATE, AND MOLECULE IMMOBILIZING SUBSTRATE

(75) Inventors: Wataru Kusaki, Jyoetsu (JP);
Toshinobu Ishihara, Jyoetsu (JP);
Takeshi Kinsho, Jyoetsu (JP); Takeru Watanabe, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 653 days.

(21) Appl. No.: 12/709,020

(22) Filed: Feb. 19, 2010

(65) Prior Publication Data

US 2010/0233827 A1 Sep. 16, 2010

(30) Foreign Application Priority Data

Mar. 11, 2009 (JP) ................................. 2009-057495

(51) Int. Cl.
| | |
|---|---|
| *G01N 33/544* | (2006.01) |
| *G01N 33/543* | (2006.01) |
| *G01N 33/53* | (2006.01) |
| *C08L 83/04* | (2006.01) |
| *C08L 83/06* | (2006.01) |

(52) U.S. Cl.
CPC ........... *G01N 33/54393* (2013.01); *C08L 83/04* (2013.01); *C08L 83/06* (2013.01); *G01N 33/54353* (2013.01); *G01N 33/543* (2013.01)

(58) Field of Classification Search
CPC .................. G01N 33/54353; G01N 33/54393; C08L 83/04; C08L 83/06; H01L 21/02214; H01L 21/02216
See application file for complete search history.

(56) References Cited

U.S. PATENT DOCUMENTS

| | | | |
|---|---|---|---|
| 5,143,854 A | 9/1992 | Pirrung et al. | |
| 5,424,186 A | 6/1995 | Fodor et al. | |
| 5,602,207 A | 2/1997 | Boyd et al. | |

(Continued)

FOREIGN PATENT DOCUMENTS

| | | |
|---|---|---|
| JP | A-4-182491 | 6/1992 |
| JP | A-4-221630 | 8/1992 |

(Continued)

OTHER PUBLICATIONS

Lofas, Stefan. Dextran modified self-assembled monolayer surfaces for use in biointeraction analysis with surface plasmon resonance. Pure & Appl. CHem, 1995, vol. 67, No. 5, pp. 829-834.*

(Continued)

*Primary Examiner* — Shafiqul Haq
(74) *Attorney, Agent, or Firm* — Oliff PLC

(57) ABSTRACT

There is disclosed a method for producing a molecule immobilizing substrate, comprising at least the steps of:
forming, on a substrate, a monomolecular film including hydroxyl groups, cyano groups, or oxiranyl groups, which are oriented toward an outmost surface of the monomolecular film; and
chemically modifying the hydroxyl groups, cyano groups, or oxiranyl groups of the monomolecular film to transform them into carboxyl groups, to thereby form, on the substrate, the monomolecular film including the carboxyl groups, which are oriented toward an outmost surface of the monomolecular film.
There can be provided: a method for producing a molecule immobilizing substrate which is free of occurrence of an immobilized-molecule peeling problem in the case of conducting an assay by immobilizing molecules on the substrate.

7 Claims, 7 Drawing Sheets

(56) References Cited

U.S. PATENT DOCUMENTS

| | | | |
|---|---|---|---|
| 5,650,474 A * | 7/1997 | Yamaya et al. | 528/12 |
| 8,293,933 B2 * | 10/2012 | Okochi | 556/419 |
| 2004/0241883 A1 | 12/2004 | Tanga et al. | |
| 2008/0125569 A1 * | 5/2008 | Wehmeyer et al. | 528/361 |
| 2008/0233409 A1 | 9/2008 | Kusaki et al. | |
| 2009/0048456 A1 * | 2/2009 | Glan et al. | 549/215 |
| 2009/0149667 A1 | 6/2009 | Okochi | |

FOREIGN PATENT DOCUMENTS

| | | |
|---|---|---|
| JP | A-08-509461 | 10/1996 |
| JP | A-2002-350447 | 12/2002 |
| JP | A-2008-518088 | 5/2008 |
| JP | A-2008-268178 | 11/2008 |
| JP | A-2009-156864 | 7/2009 |

OTHER PUBLICATIONS

Luderer et al. Immobilization of oligonucleotides for biochemical sensing by self-assembled monolayers: thiol-organic bonding on gold and silinization on silica surfaces. Top Curr Chem 2005, vol. 260, pp. 37-56.*

Li, Yunzhi et al., "Characterization of Thiol Self-Assembled Films by Laser Desorption Fourier Transform Mass Spectrometry," J. Am. Chem. Soc., 1992, vol. 114, pp. 2428-2432.

Willner, Itamar et al., "Mediated Electron Transfer in Glutathione Reductase Organized in Self-Assembled Monolayers on Au Electrodes," J. Am, Chem. Soc., 1992, vol. 114, pp. 10965-10966.

Tarlov, Michael et al., "Static Secondary Ion Mass Spectrometry of Self-Assembled Alkanethiol Monolayers on Gold," Langmuir, 1992, vol. 8, 1398-1405.

Sugimura, Hiroyuki et al., "Microfabrication Based on Self-assembled Monolayer Resists and Wet-chemical Processes," Surface Science, 2001, vol. 22, No. 6, pp. 364-369.

Oct. 2, 2012 Notification of Reasons for Refusal issued in Japanese Patent Application No. 2009-277267 (with partial English translation).

Apr. 23, 2013 Office Action issued in Japanese Patent Application No. 2009-277267 (with partial English-language Translation).

* cited by examiner

Fig. 3
(1)
(2)
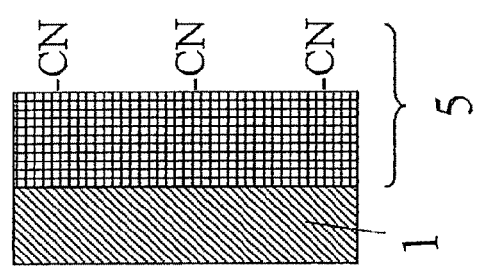
(3)
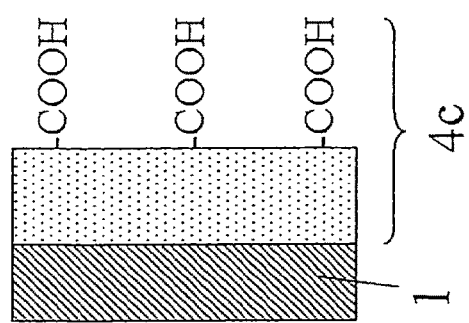

METHOD FOR PRODUCING MOLECULE IMMOBILIZING SUBSTRATE, AND MOLECULE IMMOBILIZING SUBSTRATE

BACKGROUND OF THE INVENTION

1. Field of the Invention

The present invention relates to an assay technique utilizing a biomolecule, particularly to an assay technique such as gene sequence like DNA sequence analysis and gene diagnosis, substrate biochemistry decomposition and antigen detection by an immobilized protein (enzyme, antibody), and the like, and to a method for producing a molecule immobilizing substrate to be utilized for such analyses.

2. Description of the Related Art

As methods for capturingly fixing and quantifying an antigen, antibody, or the like in a specimen, there have been adopted a western blotting method, an ELISA method, and the like. Particularly, since the ELISA method is configured to previously immobilize a particular antibody on a substrate to thereby allow for capturing of only an antigen specific to the antibody, it is made possible to detect a targeted antigen even from a specimen having a relatively lower purity.

In turn, prior examples of methods for producing substrates for immobilizing various prove molecules thereon have been known, such as an array including polypeptides arranged on a substrate (U.S. Pat. No. 5,143,854), and an array including oligonucleotides arranged on a substrate (U.S. Pat. No. 5,424,186).

Further, examples of such methods include one adopting a monomolecular film of alkanethiol so as to utilize a gold-thiol reaction for immobilizing a protein onto a substrate (J.A.C.S. 1992, 114, 10965-10966).

However, since all the prior examples have employed immobilization of molecules onto substrates by techniques such as electrostatic adsorption of molecules onto surfaces of substrates, physical adsorption of molecules into porous substrates, and chemical immobilization of molecules onto chemically unstable films, such techniques undesirably obstruct achievement of highly densified prove molecules, thereby bringing about burdens to obtainment of highly precise detecting methods.

SUMMARY OF THE INVENTION

The present invention has been carried out in view of the above circumstances, and it is therefore an object of the present invention to provide a method for producing a molecule immobilizing substrate which is free of occurrence of an immobilized-molecule peeling problem in the case of conducting an assay by immobilizing molecules on the substrate.

The present invention has been attained to achieve the above object, and provides a method for producing a molecule immobilizing substrate, comprising at least the steps of:

forming, on a substrate, a monomolecular film including hydroxyl groups, cyano groups, or oxiranyl groups, which are oriented toward an outmost surface of the monomolecular film; and chemically modifying the hydroxyl groups, cyano groups, or oxiranyl groups of the monomolecular film to transform them into carboxyl groups, to thereby form, on the substrate, the monomolecular film including the carboxyl groups, which are oriented toward an outmost surface of the monomolecular film.

In this way, by forming, on a substrate, a monomolecular film including hydroxyl groups, cyano groups, or oxiranyl groups, which are oriented toward an outmost surface of the monomolecular film, and by chemically modifying the hydroxyl groups, cyano groups, or oxiranyl groups of the monomolecular film to transform them into carboxyl groups, to thereby form, on the substrate, the monomolecular film including the carboxyl groups, which are oriented toward an outmost surface of the monomolecular film; it becomes possible to control a density, orientation, and the like of the carboxyl groups, thereby also allowing for conduction of subsequent immobilization of molecules under the uniform in-plane condition. Thus, the substrate produced by this method is allowed to prevent occurrence of a peeling problem of once immobilized molecules.

Further, the step of chemically modifying the hydroxyl groups to transform them into the carboxyl groups, can be conducted by reacting a dicarboxylic anhydride or oxidizing agent with each of the hydroxyl groups.

In this way, by reacting a dicarboxylic anhydride or oxidizing agent with each of the hydroxyl groups, it becomes possible to form, on the substrate, the monomolecular film including the carboxyl groups oriented toward an outmost surface of the monomolecular film.

Furthermore, the step of chemically modifying the cyano groups to transform them into the carboxyl groups, can be conducted by hydrolyzing the cyano groups.

In this way, by hydrolyzing the cyano groups, it becomes possible to form, on the substrate, the monomolecular film including the carboxyl groups oriented toward an outmost surface of the monomolecular film.

Moreover, the step of chemically modifying the oxiranyl groups to transform them into the carboxyl groups, can be conducted by reacting a thiol having a carboxyl group with each of the oxiranyl groups.

In this way, by reacting a thiol having a carboxyl group with each of the oxiranyl groups, it becomes possible to form, on the substrate, the monomolecular film including the carboxyl groups oriented toward an outmost surface of the monomolecular film.

Further, the method may further comprise the step of conducting addition of a sulfonic acid, in the step of reacting the thiol having a carboxyl group with each of the oxiranyl groups.

In this way, by adding a sulfonic acid in the step of reacting the thiol having a carboxyl group with each of the oxiranyl groups, it becomes possible to more readily introduce the thiol into each oxiranyl group.

Furthermore, the method may further comprise the step of reacting an acid with hydroxyl-group precursory functional groups to form, on the substrate, the monomolecular film including the hydroxyl groups, which are oriented toward an outmost surface of the monomolecular film, in the step of forming the monomolecular film on the substrate.

In this way, the transformation of the functional groups into hydroxyl groups by an acid treatment, can be conducted by exemplarily utilizing photolithography as a semiconductor fabricating method to thereby form a film containing a photoacid generator on the monomolecular film in a manner to generate an acid only at exposed portions, thereby enabling to obtain a substrate including regioselectively arranged hydroxyl groups.

Moreover, the hydroxyl-group precursory functional groups are each: an alkoxymethoxy group including an alkoxyl group moiety having 1 to 6 carbon atoms; and/or an oxiranyl group.

In this way, when the hydroxyl-group precursory functional groups are each an alkoxymethoxy group including an alkoxyl group moiety having 1 to 6 carbon atoms, and/or an oxiranyl group, the functional groups are sterically small, thereby facilitating formation of a monomolecular film. In this case, the transformation of the hydroxyl-group precursory functional groups into hydroxyl groups by reacting an acid with the hydroxyl-group precursory functional groups can be conducted, by adopting such a method: to form, on a monomolecular film, a polymer layer containing a photoacid generator; to subsequently conduct a heat treatment; to irradiate a pattern profile onto the substrate by a high energy beam; to subsequently conduct a further heat treatment; and to subsequently remove the polymer layer.

Further, the step of forming, on the substrate, the monomolecular film including hydroxyl groups, cyano groups, or oxiranyl groups, which are oriented toward an outmost surface of the monomolecular film, can be attained by immersing the substrate in a solution containing a silane compound having a hydroxyl-group precursory functional group, cyano group, or oxiranyl group.

In this way, by adopting a silane compound having a hydroxyl-group precursory functional group, cyano group, or oxiranyl group in the step of forming, on the substrate, the monomolecular film including hydroxyl groups, cyano groups, or oxiranyl groups, which are oriented toward an outmost surface of the monomolecular film: it becomes possible to form the monomolecular film more inexpensively and more readily.

Furthermore, it is preferable that the silane compound having a hydroxyl-group precursory functional group, cyano group, or oxiranyl group is a silane compound represented by the following general formula (1).

$Y_3Si—(CH_2)_m—Z$ (1)

(In the formula, "m" represents an integer of 3 to 16;

"Z" represents a hydroxyl-group precursory functional group, cyano group, or oxiranyl group; and each "Y" independently represents a halogen atom, or an alkoxyl group having 1 to 4 carbon atoms).

In this way, by adopting the silane compound represented by the general formula (1), self-organization of molecules to be immobilized can be utilized to form the monomolecular film, thereby preferably forming the monomolecular film which is dense and which includes well aligned monomolecules.

In the step of forming, on the substrate, the monomolecular film including hydroxyl groups, cyano groups, or oxiranyl groups, which are oriented toward an outmost surface of the monomolecular film, by using the silane compound represented by the general formula (1) having the hydroxyl-group precursory functional group, cyano group, or oxiranyl, group; at least one of silane compounds represented by the following general formulae (2) and (3) can be mixed with the silane compound represented by the general formula (1), and the monomolecular film can be formed by using the mixture.

$Y'_3Si—(CH_2)_n—CH_3$ (2)

$Y'_3Si—(CH_2)_n—OCH_3$ (3)

(In the formula, "n" represents an integer of 0 to "m";

"m" represents the value in the general formula (1); and each "Y'" independently represents a halogen atom, or an alkoxyl group having 1 to 4 carbon atoms).

In this way, by mixing at least one of the silane compounds represented by the general formulae (2) and (3) with the silane compound represented by the general formula (1), and by using the mixture to thereby form the monomolecular film, it becomes possible to prevent a reaction hindrance to be otherwise caused by denseness among adjacent functional groups upon chemical modification of the hydroxyl groups, cyano groups, or oxiranyl groups.

Further, in the step of forming, on the substrate, the monomolecular film including hydroxyl groups, cyano groups, or oxiranyl groups, which are oriented toward an outmost surface of the monomolecular film, by using the silane compound represented by the general formula (1) having the hydroxyl-group precursory functional group, cyano group, or oxiranyl group; a catalyst to be mixed with the silane compound represented by the general formula (1) may comprise an organic base.

In this way, by mixing the organic base as a catalyst with the silane compound, the monomolecular film formation is preferably facilitated more.

In this case, the organic base may be a pyrrolidine derivative or piperidine derivative.

In this way, by using the pyrrolidine derivative or piperidine derivative as the organic base, the monomolecular film formation is preferably facilitated furthermore.

Further, the molecule immobilizing substrate may be used to immobilize a biomolecule thereon, and the biomolecule may be a nucleic acid or protein.

In this way, the molecule immobilizing substrate can be utilized for an assay technique utilizing a biomolecule, particularly for an assay technique related to nucleic acid, protein, and the like, such as gene sequence like DNA sequence analysis and gene diagnosis, ground substrate decomposition by an immobilized protein (enzyme), and the like.

Moreover, according to the present invention, there is provided a molecule immobilizing substrate produced by any one of the above-described methods for producing a molecule immobilizing substrate.

The molecule immobilizing substrate produced by the method of the present invention is allowed to be directly contacted with an intended protein (such as enzyme or antibody) having an affinity with the carboxyl groups to thereby immobilize the protein on the molecule immobilizing substrate; and by reacting a functional group having an excellent desorbing ability such as N-hydroxy succinic acid imide to thereby esterify the carboxyl groups, and by reacting the thus esterified carboxyl groups with a substance having an intended protein, amino end, or the like, it becomes possible to immobilize the substance having the intended protein, amino end, or the like on the molecule immobilizing substrate.

As described above, by utilizing the method for producing a molecule immobilizing substrate according to the present invention, it becomes possible to readily and expediently obtain a molecule immobilizing substrate which is free of occurrence of an immobilized-molecule peeling problem in the case of conducting an assay by immobilizing molecules on the substrate.

BRIEF DESCRIPTION OF THE DRAWINGS

FIG. 3 is a schematic view of a further embodiment of a method for producing a molecule immobilizing substrate according to the present invention (Example 3);

DETAILED DESCRIPTION OF THE PREFERRED EMBODIMENTS

Figure 1:
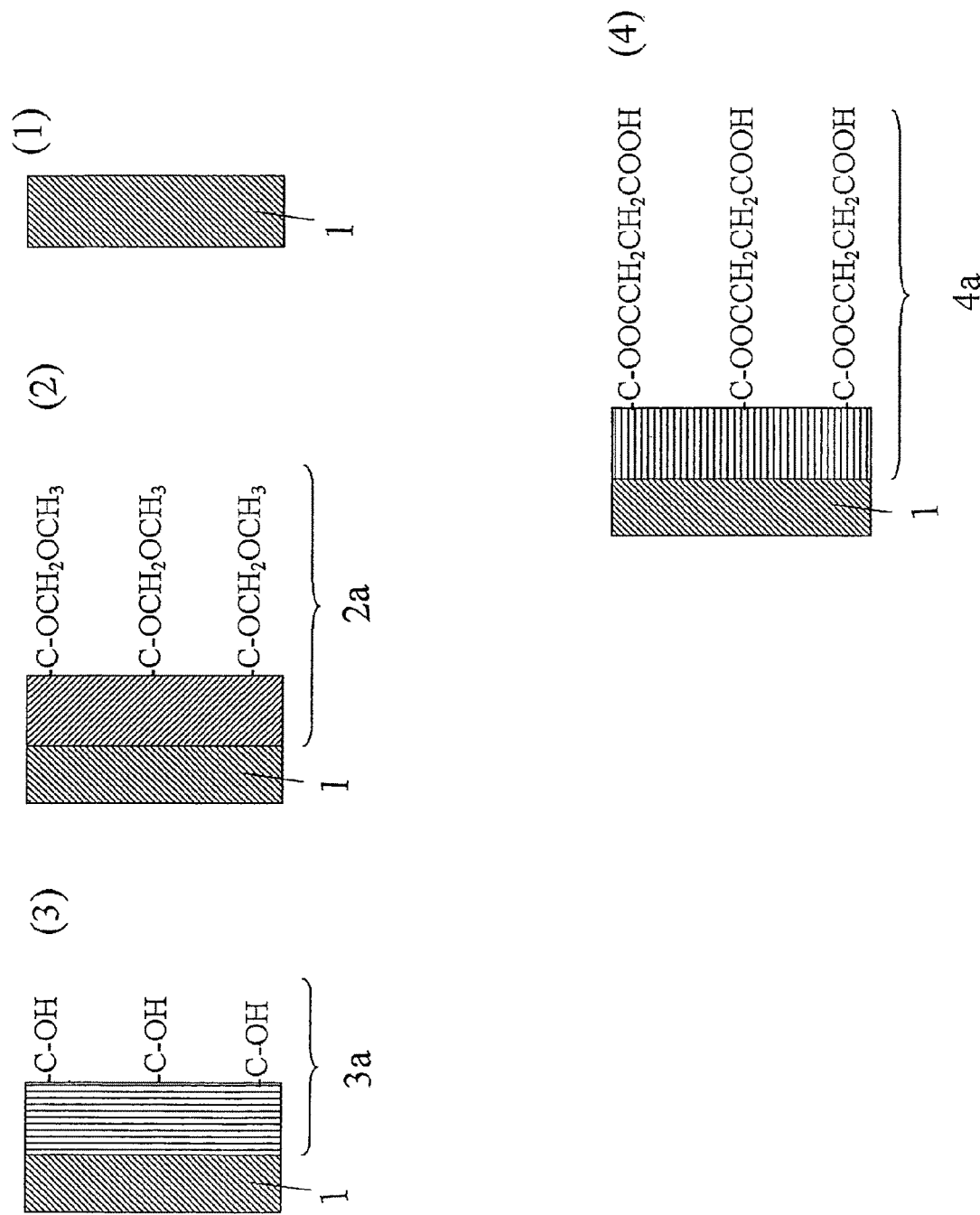
FIG. 1 is a schematic view of an embodiment of a method for producing a molecule immobilizing substrate according to the present invention (Example 1)

Although the present invention will be described with reference to embodiments thereof, the present invention is not limited thereto.

As described above, since all the conventional methods, which have been configured to conduct quantification by capturingly fixing an antigen, antibody, or the like in a specimen, have employed immobilization of molecules onto substrates by techniques such as electrostatic adsorption of molecules onto surfaces of substrates, physical adsorption of molecules into porous substrates, and chemical immobilization of molecules onto chemically unstable films, such techniques undesirably obstruct achievement of highly densified prove molecules, thereby bringing about burdens to obtainment of highly precise detecting methods.

As such, the present inventors have started development of a method for producing a molecule immobilizing substrate which is free of occurrence of an immobilized-molecule peeling problem in the case of conducting an assay by immobilizing molecules on the substrate. As a result, the present inventors have found out a method for producing a molecule immobilizing substrate, comprising at least the steps of: forming, on a substrate, a monomolecular film including hydroxyl groups, cyano groups, or oxiranyl groups, which are oriented toward an outmost surface of the monomolecular film; and chemically modifying the hydroxyl groups, cyano groups, or oxiranyl groups of the monomolecular film to transform them into carboxyl groups, to thereby form, on the substrate, the monomolecular film including the carboxyl groups, which are oriented toward an outmost surface of the monomolecular film; thereby enabling to provide the molecule immobilizing substrate having the controllable film as the monomolecular film including the carboxyl groups, which are oriented toward an outmost surface of the monomolecular film. The substrate produced by the method includes the carboxyl groups oriented toward an outmost surface of the monomolecular film, in a manner to allow for conduction of subsequent immobilization of a biological substance or the like thereto under the uniform in-plane condition, thereby enabling to avoid an immobilized-molecule peeling problem. Simultaneously, it has been confirmed that the monomolecular film formed on the substrate according to the method of the present invention, is sufficiently resistant to peeling of the monomolecular film itself. Particularly, although the noble metal (gold, silver, copper, platinum, palladium)-thiol bond is oxidized by an oxygen in an air (sulfonate formation: Langmuir, 8(5) 1398-1405, 1992, and J.A.C.S. 1992, 114, 2428-2432) to weaken the bond such that the film is peeled off, such a phenomenon is never seen in the monomolecular film to be formed on the substrate according to the method of the present invention.

Namely, the present invention provides a method for producing a molecule immobilizing substrate, comprising at least the steps of:

forming, on a substrate, a monomolecular film including hydroxyl groups, cyano groups, or oxiranyl groups, which are oriented toward an outmost surface of the monomolecular film; and chemically modifying the hydroxyl groups, cyano groups, or oxiranyl groups of the monomolecular film to transform them into carboxyl groups, to thereby form, on the substrate, the monomolecular film including the carboxyl groups, which are oriented toward an outmost surface of the monomolecular film.

The molecule immobilizing substrate produced by the method of the present invention includes the substrate and the monomolecular film formed thereon and having the carboxyl groups oriented toward an outmost surface of the monomolecular film, so that the molecule immobilizing substrate is allowed to be directly contacted with an intended protein (such as enzyme or antibody) having an affinity with the carboxyl groups to thereby immobilize the protein on the molecule immobilizing substrate. Further, by reacting a functional group having an excellent desorbing ability such as N-hydroxy succinic acid imide to thereby esterify the carboxyl groups, and by reacting the thus esterified carboxyl groups with a substance having an intended protein, amino end, or the like, it becomes possible to immobilize the substance having the intended protein, amino end, or the like on the molecule immobilizing substrate.

The molecule immobilizing substrate of the present invention produces a micro array, which can be obtained by: stamping by means of pins; a bubble jet (Registered Trade-Mark) scheme; or a method utilizing a photolithography technique.

In the step of forming, on a substrate, a monomolecular film including hydroxyl groups oriented toward an outmost surface of the monomolecular film in the present invention, the monomolecular film including the hydroxyl groups oriented toward an outmost surface of the monomolecular film can be formed on the substrate, by once forming, on the substrate, a monomolecular film including hydroxyl-group precursory functional groups oriented toward an outmost surface of the monomolecular film, and by subsequently reacting an acid with the monomolecular film including the hydroxyl-group precursory functional groups oriented toward an outmost surface of the monomolecular film.

Here, the hydroxyl-group precursory functional group used in the present specification is: a hydroxyl group protected by a so-called protective group; or a vicinal diol. Examples of such a protective group include numerous known ones, and representatively include an acyl group, oxiranyl group, acetal group, and the like. The obtained monomolecular film includes those sites to be masked in a post-process by a resist, so as to immobilize a material for recognition onto only the particular sites of the monomolecular film. Then, in the case of using a chemically amplified resist, it is preferable that the monomolecular film is not contaminated by a basic substance, and that those among the precursory functional groups are to be adopted which can be deprotected by an acidic treatment. Examples of precursory functional groups which can be deprotected under an acidic condition, include an oxiranyl group, acetal group, and the like among the above examples, and more preferably an oxiranyl group, and an alkoxymethoxy group including an alkoxyl group moiety having 1 to 6 carbon atoms. Further, the oxiranyl group, those among acetal groups which exemplarily include a methoxymethoxy group, and the like, are sterically small, thereby facilitating formation of a monomolecular film.

In cases where an outermost surface of a substrate to be subjected to immobilization is a metal oxide film upon utilizing the method of the present invention, the surface is already abundant in hydroxyl groups, thereby enabling to form a monomolecular film having silicon oxide chains by directly treating the surface by a silane compound to be described later. Further, in cases where an outermost surface layer of a substrate is a metal film, the monomolecular film can be applied thereto, by utilizing the natural oxide film at the outermost surface layer, or by oxidizing only those portions of the substrate which are near the surface layer, such as by means of an aqueous hydrogen peroxide, water, oxygen plasma, or the like. Moreover, it is conceivable to apply the monomolecular film onto a resin substrate in the case of a detecting method which does not rely on an electric method, and it has been disclosed in Japanese Patent Laid-open No. H4-221630A that a monomolecular film having a silicon oxide chain can be formed by treating a surface of the substrate by an electron beam, ion beam, or the like under an oxygen atmosphere in such a situation.

Although the monomolecular film may be formed over the whole surface of the substrate, it is typical to form the monomolecular film only at required sites, and it is possible to form a monomolecular film in a regioselective manner by using a resist film. Although the operation therefor is well known and it is unnecessary to particularly limit a resist to be used here, it is preferable to adopt a chemically amplified resist so as to conduct a selective treatment at further finer positions.

Further, as a method to form a monomolecular film only at required sites by a silane compound having a hydroxyl-group precursory functional group, cyano group, or oxiranyl group, it has been disclosed in Hiroyuki Sugimura, and Osamu Takai: "Surface Science", 22, 364 (2001) that a silane compound can be removed by irradiating an ultraviolet ray to unnecessary sites.

Concerning the step for forming, on a substrate, a monomolecular film including hydroxyl-group precursory functional groups, cyano groups, or oxiranyl groups, which are oriented toward an outmost surface of the monomolecular film, a substrate formed with a resist pattern for protecting those sites other than the sites for immobilizing molecules thereon by the above-described method, or a substrate from which unnecessary sites of a monomolecular film are to be removed by irradiation of ultraviolet ray, after formation of the monomolecular film, or an uncoated substrate which is not provided with a particular resist pattern, when the substrate is allowed to be treated over its whole surface, is to be immersed into a solution containing a silane compound such as represented by the following general formula (1), to thereby form, on the substrate, the monomolecular film including the hydroxyl-group precursory functional groups, cyano groups, or oxiranyl groups, which are oriented toward an outmost surface of the monomolecular film.

  (1)

(In the formula, "m" represents an integer of 3 to 16;
"Z" represents a hydroxyl-group precursory functional group, cyano group, or oxiranyl group; and
each "Y" independently represents a halogen atom, or an alkoxyl group having 1 to 4 carbon atoms).

Although it is possible to form a monomolecular film insofar as "m" is 3 or greater in the general formula (1), "m" is preferably 5 or greater, and more preferably 8 or greater, in the case of adopting a method to establish a space for molecules to be immobilized in a manner to be described later.

In the above, upon a modifying reaction of hydroxyl-group precursary functional groups, cyano groups, or oxiranyl groups, there is a possibility that the reaction is hindered because the functional groups (hydroxyl-group precursory functional groups, cyano groups, or oxiranyl groups) are located adjacently to one another in a crowded manner. From a standpoint to prevent such a situation, in the step of forming, on a substrate, a monomolecular film including hydroxyl groups, cyano groups, or oxiranyl groups, which are oriented toward an outmost surface of the monomolecular film, by adopting the silane compound represented by the general formula (1) having a hydroxyl-group precursory functional group, cyano group, or oxiranyl group; it is preferable to mixingly use at least one of silane compounds which are represented by the following general formulae (2) and (3), and which have alkyl chains of slightly shorter lengths, together with the silane compound represented by the general formula (1).

  (2)

  (3)

(In the formula, "n" represents an integer of 0 to "m";
"m" represents the value in the general formula (1); and
each "Y'" independently represents a halogen atom, or an alkoxy group having 1 to 4 carbon atoms).

Further, it is preferable to use the compounds represented by the general formula (2) and/or (3) in an amount of one or more by equivalent mole, and more preferably four or more by equivalent mole relative to an amount of the silane compound represented by the general formula (1). In turn, to ensure an amount of immobilization, the amount of the compounds is preferably 50 or less by equivalent mole, and more preferably 20 or less by equivalent mole the aforementioned molar quantity.

Since formation of a monomolecular film is facilitated in the step of forming, on a substrate, the monomolecular film including hydroxyl-group precursory functional groups, cyano groups, or oxiranyl groups, which are oriented toward an outmost surface of the monomolecular film according to the present invention; it is preferable that an organic base as a catalyst to be mixed together with the silane compound(s) is a nitrogen-containing organic base, and examples of the nitrogen-containing organic base include: primary, secondary, and tertiary aliphatic amines; mixed amines; aromatic amines; heterocyclic amines; nitrogen-containing compounds each having a carboxyl group; nitrogen-containing compounds each having a sulfonyl group; nitrogen-containing compounds each having a hydroxyl group; nitrogen-containing compounds each having a hydroxyphenyl group; alcoholic nitrogen-containing compounds; amides; imides; carbamates; and the like.

Specific examples of aliphatic amines may include: the primary aliphatic amines such as ammonia, methyl amine, ethyl amine, n-propyl amine, isopropyl amine, n-butyl amine, isobutyl amine, sec-butyl amine, tert-butyl amine, pentyl amine, tert-amyl amine, cyclopentyl amine, hexyl amine, cyclohexyl amine, heptyl amine, octyl amine, nonyl amine, decyl amine, dodecyl amine, cetyl amine, methylene diamine, ethylene diamine, and tetraethylene pentamine; the secondary aliphatic amines such as dimethyl amine, diethyl amine, di-n-propyl amine, diisopropyl amine, di-n-butyl amine, diisobutyl amine, di-sec-butyl amine, dipentyl amine, dicyclopentyl amine, dihexyl amine, dicyclohexyl amine, diheptyl amine, dioctyl amine, dinonyl amine, didecyl amine, didodecyl amine, dicetyl amine, N,N-dimethyl methylene diamine, N,N-dimethyl ethylene diamine, and N,N-dimethyl tetraethylene pentamine; the tertiary aliphatic amines such as trimethyl amine, triethyl amine, tri-n-propyl amine, triisopropyl amine, tri-n-butyl amine, triisobutyl amine, tri-sec-butyl amine, tripentyl amine, tricyclopentyl amine, trihexyl amine, tricyclohexyl amine, triheptyl amine, trioctyl amine, trinonyl amine, tridecyl amine, tridodecyl amine, tricetyl amine, N,N,N',N'-tetramethyl methylene diamine, N,N,N',N'-tetramethyl ethylene diamine, and N,N,N',N'-tetramethyl tetraethylene pentamine; and the like.

Examples of the mixed amines may include dimethyl ethyl amine, methyl ethyl propyl amine, benzyl amine, phenetyl amine, benzyl dimethyl amine, and the like. Specific examples of the aromatic amines and the heterocyclic amines may include aniline derivatives (such as aniline, N-methyl aniline, N-ethyl aniline, N-propyl aniline, N,N-dimethyl aniline, 2-methyl aniline, 3-methyl aniline, 4-methyl aniline, ethyl aniline, propyl aniline, trimethyl aniline, 2-nitro aniline, 3-nitro aniline, 4-nitro aniline, 2,4-dinitro aniline, 2,6-dinitro aniline, 3,5-dinitro aniline, and N,N-dimethyl toluidine), diphenyl p-tolyl)amine, methyl diphenyl amine, triphenyl amine, phenylene diamine, naphthyl amine, diaminonaphthalene, pyrrole derivatives (such as pyrrole, 2H-pyrrole, 1-methylpyrrole, 2,4-dimethylpyrrole, 2,5-dimethylpyrrole, and N-methyl pyrrole), oxazole derivatives (such as oxazole and isooxazole), thiazole derivatives (such as thiazole and isothiazole), imidazole derivatives (such as imidazole, 4-methyl imidazole, and 4-methyl-2-phenyl imidazole), a pyrazole derivative, a furazane derivative, pyrroline derivatives (such as pyrroline and 2-methyl-1-pyrroline), pyrrolidine derivatives (such as pyrrolidine, N-methyl pyrrolidine, pyrrolidinone, and N-methylpyrrolidone), an imidazoline derivative, an imidazolidine derivative, pyridine derivatives (such as pyridine, methylpyridine, ethyl pyridine, propyl pyridine, butyl pyridine, 4-(1-butylpenyl) pyridine, dimethylpyridine, trimethyl pyridine, triethyl pyridine, phenyl pyridine, 3-methyl-2-phenyl pyridine, 4-tert-butyl pyridine, diphenyl pyridine, benzyl pyridine, methoxy pyridine, butoxy pyridine, dimethoxy pyridine, 4-pyrrolidino pyridine, 2-(1-ethylpropyl) pyridine, amino pyridine, and dimethylamino pyridine), a pyridazine derivative, a pyrimidine derivative, a pyrazine derivative, a pyrazoline derivative, a pyrazolidine derivative, a piperidine derivative, a piperazine derivative, a morpholine derivative, an indole derivative, an isoindole derivative, a 1H-indazole derivative, an indoline derivative, quinoline derivatives (such as quinoline and 3-quinoline carbonitrile), an isoquinoline derivative, a cinnoline derivative, a quinazoline derivative, a quinoxaline derivative, a phthalazine derivative, a purine derivative, a pteridine derivative, a carbazole derivative, a phenanthridine derivative, an acridine derivative, a phenazine derivative, a 1,10-phenanthroline derivative, an adenine derivative, an adenosine derivative, a guanine derivative, a guanosine derivative, an uracil derivative, a uridine derivative, and the like.

Examples of the nitrogen-containing compound having a carboxyl group may include amino benzoic acid, indole carboxylic acid, amino acid derivatives (such as nicotinic acid, alanine, arginine, aspartic acid, glutamic acid, glycine, histidine, isoleucine, glycyl leucine, leucine, methionine, phenylalanine, threonine, lysine, 3-aminopyrazine-2-carboxylic acid, and methoxyalanine). Examples of the nitrogen-containing compound having a sulfonyl group may include 3-pyridine sulfonic acid, pyridinium p-toluene sulfonate, and the like. Examples of the nitrogen-containing compound having a hydroxyl group, the nitrogen-containing compound having a hydroxyphenyl group, and the alcoholic nitrogen-containing compounds may include 2-hydroxy pyridine, amino cresol, 2,4-quinoline diol, 3-indole methanol hydrate, monoethanol amine, diethanol amine, triethanol amine, N-ethyl diethanol amine, N,N-diethyl ethanol amine, triisopropanol amine, 2,2'-imino diethanol, 2-amino ethanol, 3-amino-1-propanol, 4-amino-1-butanol, 4-(2-hydroxyethyl) morpholine, 2-(2-hydroxyethyl) pyridine, 1-(2-hydroxyethyl) piperazine, 1-[2-(2-hydroxyethoxy)ethyl]piperazine, piperidine ethanol, 1-(2-hydroxyethyl) pyrrolidine, 1-(2-hydroxyethyl)-2-pyrrolidinone, 3-piperidino-1,2-propane diol, 3-pyrrolidino-1,2-propane diol, 8-hydroxy julolidine, 3-quinuclidinol, 3-tropanol, 1-methyl-2-pyrrolidine ethanol, 1-azilidine ethanol, N-(2-hydroxyethyl) phthalimide, N-(2-hydroxyethyl) isonicotinamide, and the like. Examples of the amides may include formamide, N-methyl formamide, N,N-dimethyl formamide, acetamide, N-methyl acetamide, N,N-dimethyl acetamide, propionamide, benzamide, 1-cyclohexyl pyrrolidone, and the like. Examples of the imides may include phthalimide, succinimide, maleimide, and the like. Examples of the carbamates may include N-t-butoxycarbonyl-N,N-dicyclohexyl amine, N-t-butoxycarbonyl benzimidazole, oxazolidinone, and the like.

Further, the nitrogen-containing organic compounds represented by the following general formula (C)-1 is exemplified.

$$N(X)_n(W)_{3-n'} \quad (C)\text{-}1$$

In the formula, "n"=1, 2, or 3; side-chains "X" may be the same or different, and can be expressed by the following general formulae (X1) to (X3); side-chains "W" may be the same or different, and each represents a hydrogen atom, or a linear, branched, or cyclic alkyl group having 1-20 carbon atoms, optionally containing an ether group or hydroxyl group, and "X" may be linked to form a ring(s)).

$$-R^2-O-R^3 \quad (X1)$$

$$-R^4-O-R^5-CO-R^6 \quad (X2)$$

$$-R^7-COO-R^8 \quad (X3)$$

In the general formulae (X1) to (X3), $R^2$, $R^4$, and $R^7$ represent a linear or branched alkylene group having 1-4 carbon atoms; $R^3$ and $R^6$ represent a hydrogen atom, or a linear, branched, or cyclic alkyl group having 1-20 carbon atoms, optionally containing one or more groups selected from a hydroxyl group, an ether group, an ester group, and a lactone ring. $R^5$ represents a single bond, or a linear or branched alkylene group having 1-4 carbon atoms, and $R^8$ represents a linear, branched, or cyclic alkyl group having 1-20 carbon atoms, optionally containing one or more groups selected from a hydroxyl group, an ether group, an ester group, and a lactone ring.

Specific examples of the compounds represented by the general formula (C)-1 may include, tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecan, 1-aza-12-crown-4, 1-aza-15-crown-5, 1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]

amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]ethylamine, N,N-bis(2-acetoxyethyl)-2-[(methoxycarbonyl)methoxycarbonyl]ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)ethylamine, N,N-bis(2-acetoxyethyl)-2-(tetrahydrofurfuryloxycarbonyl)ethylamine, N,N-bis(2-hydroxyethyl)-2-[(2-oxotetrahydrofuran-3-yl)oxycarbonyl]ethylamine, N,N-bis(2-acetoxyethyl)-2-[(2-oxotetrahydrofuran-3-il)oxycarbonyl]ethylamine, N,N-bis(2-hydroxyethyl)-2-(4-hydroxybutoxycarbonyl)ethylamine, N,N-bis(2-formyloxyethyl)-2-(4-formyloxybutoxycarbonyl)ethylamine, N,N-bis(2-formyloxyethyl)-2-(2-formyloxyethoxycarbonyl)ethylamine, N,N-bis(2-methoxyethyl)-2-(methoxycarbonyl)ethylamine, N-(2-hydroxyethyl)bis[2-(methoxycarbonyl)ethyl]amine, N-(2-acetoxyethyl)bis[2-(methoxycarbonyl)ethyl]amine, N-(2-hydroxyethyl)bis[2-(ethoxycarbonyl)ethyl]amine, N-(2-acetoxyethyl)bis[2-(ethoxycarbonyl)ethyl]amine, N-(3-hydroxy-1-propyl)bis[2-(methoxycarbonyl)ethyl]amine, N-(3-acetoxy-1-propyl)bis[2-(methoxycarbonyl)ethyl]amine, N-(2-methoxyethyl)bis[2-(methoxycarbonyl)ethyl]amine, N-butylbis[2-(methoxycarbonyl)ethyl]amine, N-butylbis[2-(2-methoxyethoxycarbonyl)ethyl]amine, N-methylbis(2-acetoxyethyl)amine, N-ethylbis(2-acetoxyethyl)amine, N-methylbis(2-pivaloyloxyethyl)amine, N-ethylbis[2-(methoxycarbonyloxy)ethyl]amine, N-ethylbis[2-(tert-butoxycarbonyloxy)ethyl]amine, tris(methoxycarbonylmethyl)amine, tris(ethoxycarbonylmethyl)amine, N-butylbis(methoxycarbonylmethyl)amine, N-hexylbis(methoxycarbonylmethyl)amine, β-(diethylamino)-δ-valerolactone, and the like.

Further, the nitrogen-containing organic bases, having a cyclic structure, represented by the following general formula (C)-2 is exemplified.

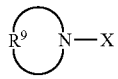
(c)-2

In the formula, "X" is as defined above, $R^9$ represents a linear, or branched alkylene group having 2-20 carbon atoms, optionally containing one or more groups selected from a carbonyl group, an ether group, an ester group, and a sulfide group.

Specific examples of the compound represented by the general formula (C)-2 may include 1-[2-(methoxymethoxy)ethyl]pyrrolidine, 1-[2-(methoxymethoxy)ethyl]piperidine, 4-[2-(methoxymethoxy)ethyl]morpholine, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, acetoxy 2-morpholinoethyl acetate, methoxy 2-(1-pyrrolidinyl)ethyl acetate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino)propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl)propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butylolactone, β-piperidino-γ-butylolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, 2-methoxyethyl morpholinoacetate, 2-morpholinoethyl 2-methoxyacetate, 2-morpholinoethyl 2-(2-methoxyethoxy)acetate, 2-morpholinoethyl 2-[2-(2-methoxyethoxy)ethoxy]acetate, 2-morpholinoethyl hexanoate, 2-morpholinoethyl octanoate, 2-morpholinoethyl decanoate, 2-morpholinoethyl laurate, 2-morpholinoethyl myristate, 2-morpholinoethyl palmitate, 2-morpholinoethyl stearate, and the like.

Further, the nitrogen-containing organic bases, having a cyano group(s), represented by the following general formulae (C)-3 to (C)-6 are exemplified.

(C)-3

(C)-4

(C)-5

(C)-6

In the formulae, "X", $R^9$, and "n'" are as defined above, $R^{10}$ and $R^{11}$ may be the same or different, and represent a linear or branched alkylene group having 1-4 carbon atoms.

Specific examples of the nitrogen-containing organic base having a cyano group represented by the above formulae (C)-3 to (C)-6 may include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropionate, methyl N-(2-cyanoethyl)-N-(2-hydroxyethyl)-3-aminopropionate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-(methoxymethoxy)ethyl]-3-aminopropiononitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiononitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl)aminoacetonitrile, N,N-bis(2-acetoxyethyl)aminoacetonitrile, N,N-bis(2-formyloxyethyl)aminoacetonitrile, N,N-bis(2-methoxyethyl)aminoacetonitrile, N,N-bis[2-(methoxymethoxy)ethyl]aminoacetonitrile, methyl N-cyanomethyl-N-(2-methoxyethyl)-3-aminopropionate, methyl N-cyanomethyl-N-(2-hydroxyethyl)-3-aminopropionate, methyl N-(2-acetoxyethyl)-N-cyanomethyl-3-aminopropionate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl]aminoacetonitrile, N-(cyanomethyl)-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl)aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)ethyl]-3-aminopropionate, (2-cyanoethyl) 3-diethylaminopropionate, (2-cyanoethyl) N,N-bis(2-hydroxyethyl)-3-aminopropionate, (2-cyanoethyl) N,N-bis(2-acetoxyethyl)-3-aminopropionate, (2-cyanoethyl) N,N-bis(2-formyloxyethyl)-3-aminopropionate, (2-cyanoethyl) N,N-bis(2-methoxyethyl)-3-aminopropionate, (2-cyanoethyl) N,N-bis[2-(methoxymethoxy)ethyl-3-aminopropionate, cyanomethyl 1-pyrrolidinepropionate, cyanomethyl 1-piperidinepropionate, cyanomethyl 4-morpholinepropionate, (2-cyanoethyl) 1-pyrrolidinepropionate, (2-cyanoethyl) 1-piperidinepropionate, (2-cyanoethyl) 4-morpholinepropionate, and the like.

Further, the nitrogen-containing organic bases, having an imidazole skeleton and a polar functional group, represented by the following general formula (C)-7 is exemplified.

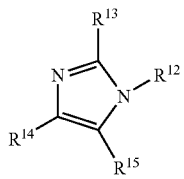

(C)-7

In the formula, $R^{12}$ represents a linear, branched, or cyclic alkyl group having 2-20 carbon atoms, and containing any one or more of polar functional groups selected from a hydroxyl group, a carbonyl group, an ester group, an ether group, a sulfide group, a carbonate group, a cyano group and an acetal group; $R^{13}$, $R^{14}$, and $R^{15}$ each represents a hydrogen atom, a linear, branched, or cyclic alkyl group having 1-10 carbon atoms, an aryl group, or an aralkyl group).

Further, the nitrogen-containing organic bases, having a benzimidazole skeleton and a polar functional group, represented by the following general formula (C)-8 is exemplified.

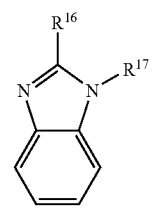

(C)-8

In the formula, $R^{16}$ represents a hydrogen atom, a linear, branched, or cyclic alkyl group having 1-10 carbon atoms, an aryl group, or an aralkyl group; $R^{17}$ represents a linear, branched, or cyclic alkyl group having 1-20 carbon atoms, and containing any one or more of polar functional groups selected from an ester group, an acetal group, and a cyano group, and in addition, optionally containing any one or more of groups selected from a hydroxyl group, a carbonyl group, an ether group, a sulfide group, and a carbonate group.

Further, the nitrogen-containing heterocyclic compounds, having a polar functional group represented, by the following general formulae (C)-9 and (C)-10 are exemplified.

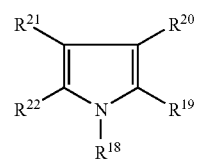

(C)-9

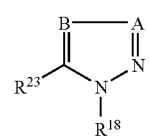

(C)-10

In the formulae, "A" represents a nitrogen atom or =C—$R^{24}$; "B" represents a nitrogen atom or =C—$R^{25}$; $R^{18}$ represents a linear, branched, or cyclic alkyl group having 2-20 carbon atoms, and containing one or more of polar functional groups selected from a hydroxyl group, a carbonyl group, an ester group, an ether group, a sulfide group, a carbonate group, a cyano group, and an acetal group; $R^{19}$, $R^{20}$, $R^{21}$, and $R^{22}$ each represents a hydrogen atom, a linear, branched, or cyclic alkyl group having 1-10 carbon atoms, or an aryl group, or $R^{19}$ and $R^{20}$, and $R^{21}$ and $R^{22}$ each may be linked to form a benzene ring, a naphthalene ring, or a pyridine ring; $R^{23}$ represents a hydrogen atom, a linear, branched, or cyclic alkyl group having 1-10 carbon atoms, or an aryl group; $R^{24}$ and $R^{25}$ each represents a hydrogen atom, a linear, branched, or cyclic alkyl group having 1-10 carbon atoms, or an aryl group; and $R^{23}$ and $R^{25}$ may be linked to form a benzene ring or a naphthalene ring.

Further, the nitrogen-containing organic bases, having an aromatic carboxylic acid ester structure, represented by the following general formulae (C)-11 to (C)-14 are exemplified.

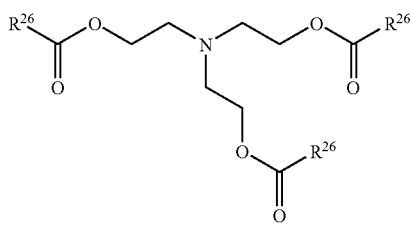
(C)-11

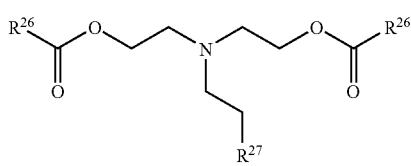
(C)-12

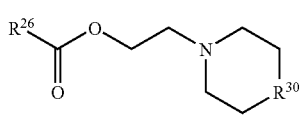
(C)-13

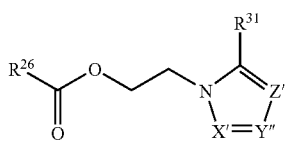
(C)-14

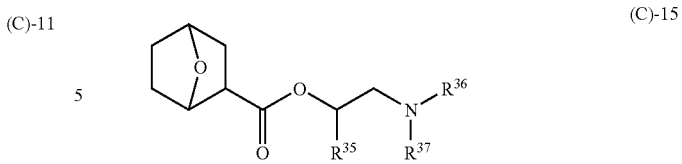
(C)-15

In the formula, $R^{35}$ represents a hydrogen atom, or a linear, branched, or cyclic alkyl group having 1-10 carbon atoms; each $R^{36}$ and $R^{37}$ independently represents an alkyl group having 1-20 carbon atoms, an aryl group having 6-20 carbon atoms, or an aralkyl group having 7-20 carbon atoms, and optionally containing the group may comprise one or more of polar functional groups such as an ether, a carbonyl, an ester, an alcohol, a thio group, a nitrile, an amine, an imine, an amide, wherein a part of the hydrogen atoms may be substituted by a halogen atom; and $R^{36}$ and $R^{37}$ may be linked to form a heterocyclic ring, or heteroaromatic ring having 2-20 carbon atoms.

The nitrogen-containing organic base used as the catalyst contained in a mixture along with the silane compound(s) is preferably, among the above nitrogen-containing organic bases, the nitrogen-containing organic base containing the following structural formula (C)-16.

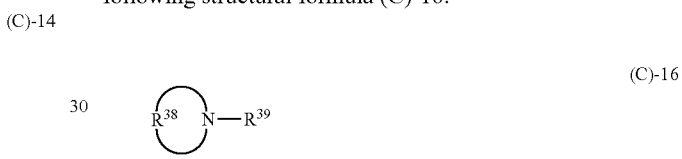
(C)-16

In the formula, $R^{38}$ represents a linear, cyclic or branched alkylene group having 2-20 carbon atoms, and optionally containing one or more groups selected from a carbonyl group, an ether group, an ester group, and a sulfide group; and $R^{39}$ represents a hydrogen atom, a linear or branched alkyl group having 1-25 carbon atoms, and optionally containing one or more groups selected from a hydroxyl group, a carbonyl group, an ether group, an ester group and a lactone ring.

Concerning condensation of a silane compound, it is known that the condensation can be particularly promoted more rapidly by making it to be basic in a water solution. However, the action of the base in an organic solvent is not well known. Nonetheless, according to the investigation of the present invention, it has been revealed that the monomolecular film formation is further facilitated by adopting the above nitrogen-containing organic base having the cyclic structure.

Moreover, by a further investigation, it has been revealed that the monomolecular film formation is more facilitated by adopting a pyrrolidine derivative or piperidine derivative as the nitrogen-containing organic base.

That is, the nitrogen-containing organic base is more preferably the pyrrolidine derivative and the piperidine derivative, and still more preferably pyrrolidine, N-methylpyrrolidine, piperidine and N-methylpiperidine are exemplified. However, the nitrogen-containing organic base is not limited thereto.

Examples of the solvents used when the monomolecular film including hydroxyl-group precursory functional groups, cyano groups, or oxiranyl groups, which are oriented toward an outmost surface of the monomolecular film is formed according to the present invention may include: ketones such as cyclohexanone and methyl-2-n-amyl ketone; alcohols such as 3-methoxybutanol, 3-methyl-3-methoxybutanol, In the formulae, $R^{26}$ represents an aryl group having 6-20 carbon atoms, or a heteroaromatic group having 4-20 carbon atoms, and a part or all of the hydrogen atoms thereof may be substituted by a halogen atom, a linear, branched or cyclic alkyl group having 1-20 carbon atoms, an aryl group having 6-20 carbon atoms, an aralkyl group having 7-20 carbon atoms, an alkoxy group having 1-10 carbon atoms, an acyloxy group having 1-10 carbon atoms, or an alkylthio group having 1-10 carbon atoms; $R^{27}$ represents $CO_2R^{28}$, $OR^{29}$, or a cyano group; $R^{28}$ represents an alkyl group having 1-10 carbon atoms whose methylene group may be partly substituted by an oxygen atom; $R^{29}$ represents an alkyl or acyl group having 1-10 carbon atoms whose methylene group may be partly substituted by an oxygen atom; $R^{30}$ represents a single-bond, a methylene group, an ethylene group, a sulfur atom, or —O(CH$_2$CH$_2$O)$_{n'''}$— group; "n'''" represents 0, 1, 2, 3, or 4; $R^{31}$ represents a hydrogen atom, a methyl group, an ethyl group, or a phenyl group; "X'''" represents a nitrogen atom, or $CR^{32}$; "Y'''" represents a nitrogen atom, or $CR^{33}$; "Z'''" represents a nitrogen atom, or $CR^{34}$; and each $R^{32}$, $R^{33}$, and $R^{34}$ independently represents, of each other, a hydrogen atom, a methyl group, or a phenyl group, or $R^{32}$ and $R^{33}$, or $R^{33}$ and $R^{34}$ may be linked to form an aromatic ring having 6-20 carbon atoms, or a heteroaromatic ring having 2-20 carbon atoms.

Further, the nitrogen-containing organic bases, having a 7-oxanorbornane-2-carboxylate ester structure and represented by the following general formula (C)-15 is exemplified.

1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; lactones such as γ-butylolactone; hydrocarbons such as n-hexane and n-nonane; aromatics such as benzene and toluene; chloroform; and the like. These solvents may be used alone or in mixture of two or more, but the solvent is not limited thereto.

To form, on a substrate, a monomolecular film including hydroxyl-group precursory functional groups, cyano groups, or oxiranyl groups, which are oriented toward an outmost surface of the monomolecular film, by the silane compound having a hydroxyl-group precursory functional group, cyano group, or oxiranyl group; the silane compound represented by the general formula (1), or a mixture of the silane compound represented by the general formula (1) with at least one of the silane compounds represented by the general formulae (2) and (3), is exemplarily prepared into a relatively dilute solution in a concentration range of $2.0 \times 10^{-2}$ to $5.0 \times 10^{-2}$ mole/L by using a solvent having an extremely low polarity, and the nitrogen-containing organic base therein is adjusted to exemplarily have a concentration of $2.0 \times 10^{-2}$ to $5.0 \times 10^{-2}$ mole/L; and a coating targeted substrate, which may be covered by a resist at those sites where coating is desired to be avoided, is immersed in the solution for about 24 hours in the case of adopting a triethoxysilane compound, for example.

In the present invention, it is particularly preferable that the concentration ratio of the silane compound(s) and the nitrogen-containing organic base is made to exhibit such a mole ratio that the nitrogen-containing organic base is 0.1 to 100 moles relative to 1 mole of the silane compound(s).

After the above treatment, in cases where monomolecular film formation has been conducted in a site-selective manner by using a resist film, the resist pattern is to be removed by an organic solvent such as propylene glycol monomethyl ether, ethyl lactate, or the like which is to be typically used upon preparation of a resist solution and which is capable of dissolving a resist film, thereby enabling to obtain a substrate including hydroxyl-group precursory functional groups, cyano groups, or oxiranyl groups, which are oriented toward its outmost surface.

Although the substrate can be immersed in an acidic solution such as hydrochloric acid, sulfuric acid, or the like so as to transform the hydroxyl-group precursory functional groups into hydroxyl groups in cases where the monomolecular film including the hydroxyl-group precursory functional groups oriented toward an outmost surface of the monomolecular film has been formed on the substrate by the method of the present invention, it is also possible to immerse the substrate in an acidic solution obtained by dissolving an organic acid such as p-toluenesulfonic acid or methanesulfonic acid into an organic solvent, and to heat it then.

After the above treatment, the treated substrate is immersed into a solution of dicarboxylic anhydride compound or a solution containing an oxidizing agent, thereby enabling to obtain a substrate having carboxyl groups oriented toward its outmost surface. At that time, in the case of adopting the solution of dicarboxylic anhydride compound, the concentration of the dicarboxylic anhydride is desirably 0.001 mole/L or higher, and in the case of adopting the solution containing an oxidizing agent, it is desirable to appropriately adjust the concentration thereof depending on a rate of oxidation.

After the treatment, the molecule immobilizing substrate including carboxyl groups oriented toward its outmost surface is completed.

Upon utilization of the method of the present invention, the dicarboxylic anhydrides to be used may each include one or more double bonds in its carbon chain, or may each include a ring. These compounds may each have a side-chain substituted by a methyl group, ethyl group, halogen atom, hydroxyl group, cyano group, nitro group, carbonyl group, carboxyl group, or the like.

Examples of the dicarboxylic anhydride of the present invention include succinic anhydride, glutaric anhydride, adipic anhydride, pimelic anhydride, suberic anhydride, azelaic anhydride, sebacic anhydride, cyclohexane-1,2-dicarboxylic anhydride, norbornene-1,2-dicarboxylic anhydride, norbornane-1,2-dicarboxylic anhydride, phthalic anhydride, 1,2-naphthalenedicarboxylic anhydride, 1,8-naphthalenedicarboxylic anhydride, tartaric anhydride, diacetyltartaric anhydride, methylsuccinic anhydride, ethylsuccinic anhydride, butylsuccinic anhydride, 4-bromophthalic anhydride, 4-chlorophthalic anhydride, 4-methylphthalic anhydride, 4-ethynylphthalic anhydride, 4-nitrophthalic anhydride, 4-carboxyphthalic anhydride, itaconic anhydride, and the like. These dicarboxylic anhydrides may be used alone or in mixture of two or more, but the dicarboxylic anhydride is not limited thereto.

Examples of the solvent used for the step of reacting the dicarboxylic anhydride include: water; ketones such as cyclohexanone and methyl-2-n-amyl ketone; alcohols such as methanol, ethanol, 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; lactones such as γ-butylolactone; hydrocarbons such as n-hexane and n-nonane; aromatics such as benzene and toluene; chloroform; and the like. These solvents may be used alone or in mixture of two or more, but the solvent is not limited thereto.

Examples of the oxidizing agent of the present invention include: halogen oxo acids such as hypochlorous acid, chlorous acid, chloric acid, perchloric acid, bleaching powder, hypobromous acid, bromous acid, bromic acid, perbromic acid, hypoiodous acid, iodous acid, iodic acid, periodic acid; oxo acids of phosphorus such as phosphorous acid, phosphonic acid, phosphoric acid, perphosphoric acid; oxo acids of nitrogen such as nitrous acid, nitric acid; oxo acids of sulfur such as sulfurous acid, sulfuric acid; oxo acids of transition element such as chromic acid, dichromic acid, chromic acid mixture, pyridinium chlorochromate, pyridinium dichromate, manganic acid, permanganic acid; salt of these acids; and the like. These oxidizing agents may be used alone or in mixture of two or more, but the oxidizing agent is not limited thereto.

Examples of the solvent used for the step of reacting the oxidizing agent with the hydroxyl groups in the present invention include: water; alcohols such as methanol, ethanol, 3-methoxybutanol, 3-methyl-3-methoxybutanol, 1-methoxy-2-propanol, 1-ethoxy-2-propanol; ketones such as acetone, cyclohexanone, methyl-2-n-amylketone; aromatic such as pyridine; amidos such as dichloromethane, formamide, acetamide, N,N-dimethylformamide; organic solvents such as chloroform; and the like. However, to bring oxidative reaction under control, the solvent can appropriately be selected and mixed, mainly water is principal solution.

When a monomolecular film including cyano groups oriented toward an outmost surface of the monomolecular film is formed on a substrate by the method of the present invention, it is possible to obtain the substrate having monomolecular film including carboxyl groups oriented toward an outmost surface of the monomolecular film, by hydrolyzing the cyano groups. At that time, it is preferable to conduct the hydrolysis under a strong acidic condition, and it is then possible to use hydrochloric acid or sulfuric acid, more preferably hydrochloric acid. The concentration of hydrochloric acid at this time is desirably to be appropriately adjusted from both standpoints of a progressing degree of hydrolysis of cyano groups and avoidance of peeling of the monomolecular film, and it is exemplarily possible to use concentrated hydrochloric acid by diluting it at a dilution ratio of 0 to 10.

When a monomolecular film including oxiranyl groups oriented toward an outmost surface of the monomolecular film is formed on a substrate by the method of the present invention, it is possible to obtain the substrate having monomolecular film including carboxyl groups oriented toward an outmost surface of the monomolecular film, by immersing the treated substrate into a solution containing a thiol having a carboxyl group. At that time, the concentration of the thiol is desirably $2.0 \times 10^{-2}$ to 4 mole/L, more desirably 0.1 to 1 mole/L. In this case, it is also possible to further add a sulfonic acid at a mole ratio of 0.001 to 1 into the solution containing the thiol having a carboxyl group.

After the treatment, the molecule immobilizing substrate including carboxyl groups oriented toward its outmost surface is completed.

Examples of the thiol having a carboxyl group of the present invention include thioglycolic acid, 2-mercaptopropionic acid, 3-mercaptopropionic acid, mercaptosuccinic acid, 2-mercaptobenzoic acid, 3-mercaptobenzoic acid, 4-mercaptobenzoic acid, and the like. These thiols may be used alone or in mixture of two or more, but the thiol is not limited thereto.

Examples of the sulfonic acid of the present invention include methanesulfonic acid, ethanesulfonic acid, 2-hydroxyethanesulfonic acid, 2-mercaptoethanesulfonic acid, trifluoromethanesulfonic acid, pentafluoroethanesulfonic acid, heptafluoropropanesulfonic acid, nonafluorobutanesulfonic acid, benzenesulfonic acid, p-toluenesulfonic acid, 10-camphorsulfonic acid, and the like. These sulfonic acids may be used alone or in mixture of two or more, but the sulfonic acid is not limited thereto Examples of the solvent used for the step of reacting the thiol having a carboxyl group with the oxiranyl groups in the present invention include: water; ketones such as cyclohexanone and methyl-2-n-amyl ketone; alcohols such as methanol, ethanol, 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether and diethylene glycol dimethyl ether; cyclic ethers such as 1,2-dioxane, 1,3-dioxane, 1,4-dioxane, oxetane, tetrahydrofuran, and tetrahydropyran; esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; lactones such as γ-butyrolactone; hydrocarbons such as n-hexane and n-nonane; aromatics such as benzene and toluene; chloroform; and amides such as formamide, acetamide, and N,N-dimethylformamide; and the like. These solvents may be used alone or in mixture of two or more, but the solvent is not limited thereto

EXAMPLE

The present invention will be described further in detail with reference to Examples and Comparative Examples. However, the present invention is not limited by the following Examples.

Production Example 1

Production of 10-(methoxymethoxy)decyltrimethoxysilane

Under a nitrogen atmosphere at 80° C., a mixture of 64 g of trimethoxysilane and 0.57 g of acetic acid was dropped in a mixture of 100 g of 10-(methoxymethoxy)-1-decene and a catalytic amount of a solution of tetrahydrofuran chloroplatinate. The resultant mixture was stirred for 3 hours at 80° C., and then the reaction mixture was distilled under reduced pressure, to obtain 131 g of an intended substance.

10-(methoxymethoxy)decyltrimethoxysilane

Boiling point: 142° C./66 Pa
IR (liquid film) vmax: 2927, 2854, 2840, 1465, 1191, 1143, 1089, 1049 $cm^{-1}$.
$^{13}$C-NMR (150 MHz, $CDCl_3$) δ: 9.10, 22.55, 26.18, 29.19, 29.39, 29.56, 29.71, 33.09, 50.44, 55.03, 67.84, 96.34 ppm.
$^1$H-NMR (600 MHz, $CDCl_3$) δ: 0.59-0.62 (2H, m), 1.21-1.39 (14H, m), 1.52-1.57 (2H, quintet-like), 3.32 (3H, s), 3.48 (2H, t, J=7 Hz), 3.53 (9H, s), 4.58 (2H, s) ppm.

Production Example 2

Production of Jones Reagent 80 g of chromic acid and 88 ml of concentrated sulfuric acid were added in 400 ml of pure water, and then the resultant mixture was stirred, to obtain an intended reagent.

Production Example 3

Production of 11,12-epoxydodecyltrimethoxysilane

It was produced according to the method of Japanese Patent Laid-open No. H4-182491.

11,12-epoxydodecyltrimethoxysilane

IR (liquid film) vmax: 3041, 2925, 2854, 2840, 1727, 1465, 1911, 1089, 916 $cm^{-1}$.
$^{13}$C-NMR (150 MHz, $CDCl_3$) δ: 9.10, 22.54, 25.92, 29.18, 29.39, 29.40, 29.42, 29.48, 32.45, 33.08, 47.07, 50.42, 52.35 ppm.
$^1$H-NMR (600 MHz, $CDCl_3$) δ: 0.59-0.62 (2H, m), 1.20-1.51 (20H, m), 2.421 (1H, dd, J=3.5 Hz), 2.70 (1H, t-like, J=5 Hz), 2.85-2.88 (1H, m) ppm.

Example 1

As shown in FIG. 1(1), a substrate 1 having a silicon oxide film on its surface was immersed into chloroform and then into acetone, followed by ultrasonic cleaning; and then immersed into a piranha solution for 15 minutes, then into water for 1 hour, and further into a toluene solution containing 0.02 mole/L of the 10-(methoxymethoxy)decyltrimethoxysilane obtained in Production Example 1 and 0.02 mole/L of piperidine for 12 hours, thereby forming, on the substrate, a monomolecular film 2a including methoxymethoxy groups oriented toward an outmost surface of the monomolecular film (FIG. 1(2)). The thus obtained substrate was immersed into chloroform, subsequently into acetone, and then into water, together with ultrasonic cleaning for 5 minutes in each medium. The above treated substrate was immersed into concentrated hydrochloric acid for 12 hours to deprotect the methoxymethoxy groups of the monomolecular film 2a, thereby forming, on the substrate, a monomolecular film 3a including hydroxyl groups oriented toward an outmost surface of the monomolecular film (FIG. 1(3)). Thereafter, the resultant substrate was rinsed by pure water, and then dried in dry air. Next, the resultant substrate was immersed into a pyridine solution containing 1 mole/L of succinic acid anhydride for 12 hours, thereby forming, on the substrate, a monomolecular film 4a including carboxyl groups oriented toward an outmost surface of the monomolecular film (FIG. 1(4)). The resultant substrate was cleaned by water, and then by methanol, followed by drying in dry air.

Example 2

Figure 2:
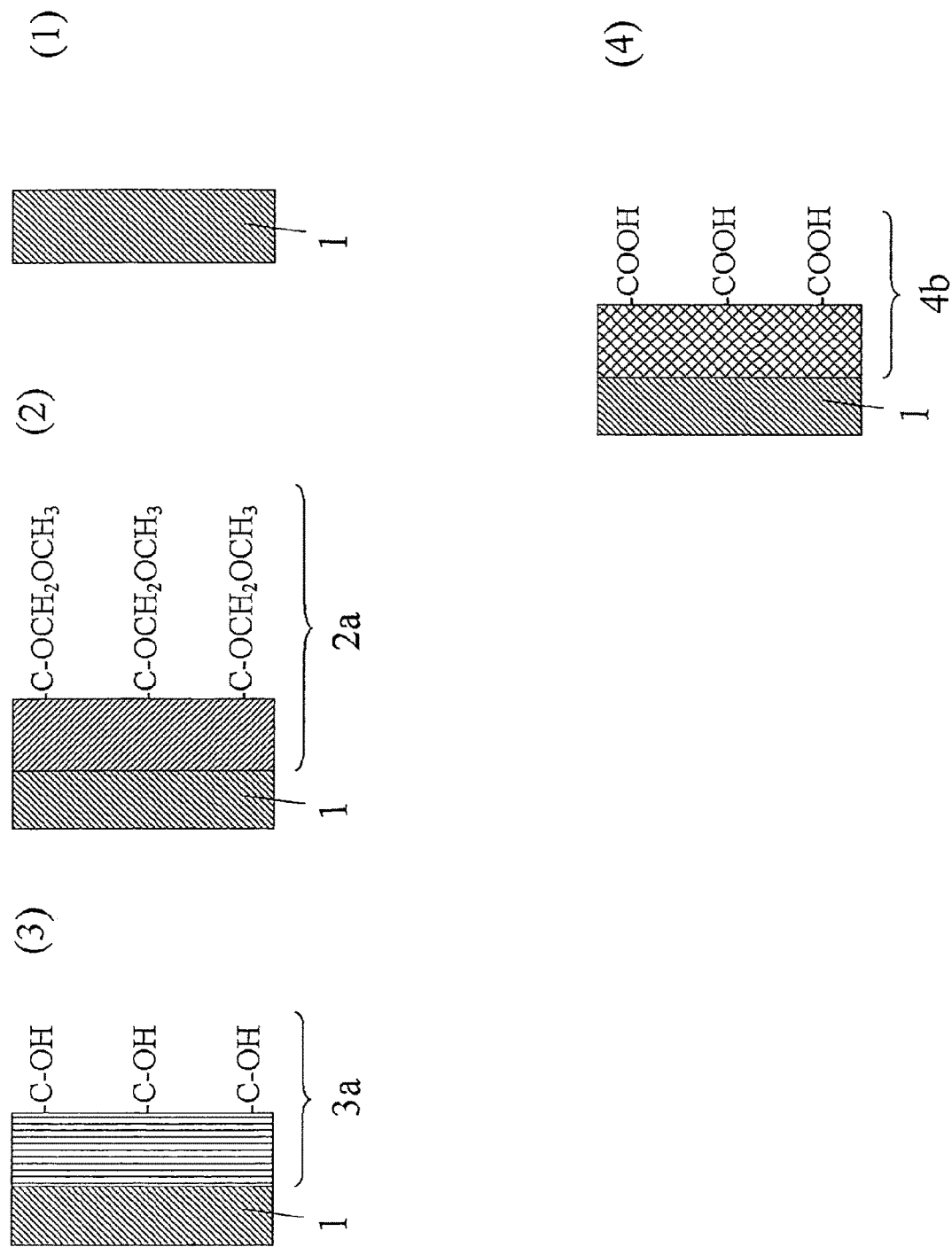
FIG. 2 is a schematic view of another embodiment of a method for producing a molecule immobilizing substrate according to the present invention (Example 2)

As shown in FIG. 2(1), a substrate 1 having a silicon oxide film on its surface was immersed into chloroform and then into acetone, followed by ultrasonic cleaning; and then immersed into a piranha solution for 15 minutes, then into water for 1 hour, and further into a toluene solution containing 0.02 mole/L of the 10-(methoxymethoxy)decyltrimethoxysilane obtained in Production Example 1 and 0.02 mole/L of piperidine for 12 hours, thereby forming, on the substrate, a monomolecular film 2a including methoxymethoxy groups oriented toward an outmost surface of the monomolecular film (FIG. 2(2)). The thus obtained substrate was immersed into chloroform, subsequently into acetone, and then into water, together with ultrasonic cleaning for 5 minutes in each medium. The above treated substrate was immersed into concentrated hydrochloric acid for 12 hours to deprotect the methoxymethoxy groups of the monomolecular film 2a, thereby forming, on the substrate, a monomolecular film 3a including hydroxyl groups oriented toward an outmost surface of the monomolecular film (FIG. 2(3)). The resultant substrate was rinsed by pure water, and then dried in dry air. Next, the resultant substrate was immersed for 20 minutes into a solution prepared by mixing acetone at a volume ratio of 2,000 relative to and with the Jones reagent as an oxidizing agent obtained in Production Example 2, thereby forming, on the substrate, a monomolecular film 4b including carboxyl groups oriented toward an outmost surface of the monomolecular film (FIG. 2(4)). The resultant substrate was cleaned by water, and then by methanol, followed by drying in dry air.

Example 3

As shown in FIG. 3(1), a substrate 1 having a silicon oxide film on its surface was immersed into chloroform and then into acetone, followed by ultrasonic cleaning; and then immersed into a piranha solution for 15 minutes, then into water for 1 hour, and further into a toluene solution containing 0.02 mole/L of 11-nitrileundecyltrimethoxysilane (made by Gelest Inc.) and 0.02 mole/L of piperidine for 12 hours, thereby forming, on the substrate, a monomolecular film 5 including cyano groups oriented toward an outmost surface of the monomolecular film (FIG. 3(2)). The thus obtained substrate was immersed into chloroform, subsequently into acetone, and then into water, together with ultrasonic cleaning for 5 minutes in each medium. The above treated substrate was immersed into a solution of concentrated hydrochloric acid:water=1:1 at 80° C. and heated for 4 hours to hydrolyze the cyano groups, thereby forming, on the substrate, a monomolecular film 4c including carboxyl groups oriented toward an outmost surface of the monomolecular film (FIG. 3(3)). The resultant substrate was cleaned by water, and then by methanol, followed by drying in dry air.

Example 4

Figure 4:
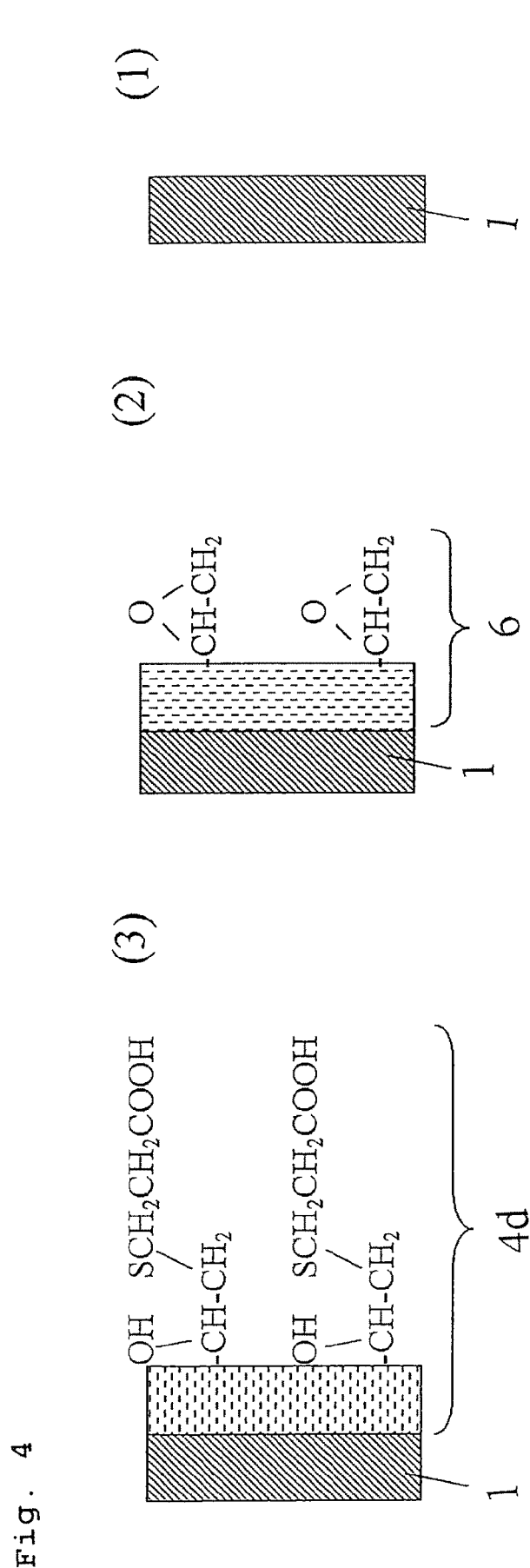
FIG. 4 is a schematic view of still another embodiment of a method for producing a molecule immobilizing substrate according to the present invention (Example 4)

As shown in FIG. 4(1), a substrate 1 having a silicon oxide film on its surface was immersed into chloroform and then into acetone, followed by ultrasonic cleaning; and then immersed into a piranha solution for 15 minutes, then into water for 1 hour, and further into a toluene solution containing 0.02 mole/L of 11,12-epoxydodecyltrimethoxysilane obtained in Production Example 3 and 0.02 mole/L of piperidine for 12 hours, thereby forming, on the substrate, a monomolecular film 6 including oxiranyl groups oriented toward an outmost surface of the monomolecular film (FIG. 4(2)). The thus obtained substrate was immersed into chloroform, subsequently into acetone, and then into water, together with ultrasonic cleaning for 5 minutes in each medium. The above treated substrate was immersed into a toluene solution containing 1 mole/L of 3-mercaptopropionic acid and 0.0018 mole/L of methanesulfonic acid for 12 hours, thereby forming, on the substrate, a monomolecular film 4d including carboxyl groups oriented toward an outmost surface of the monomolecular film (FIG. 4(3)). The resultant substrate was subjected to ultrasonic cleaning in toluene for 1 minute, and further cleaned by acetone and then by water, followed by drying in dry air.

Example 5

Figure 5:
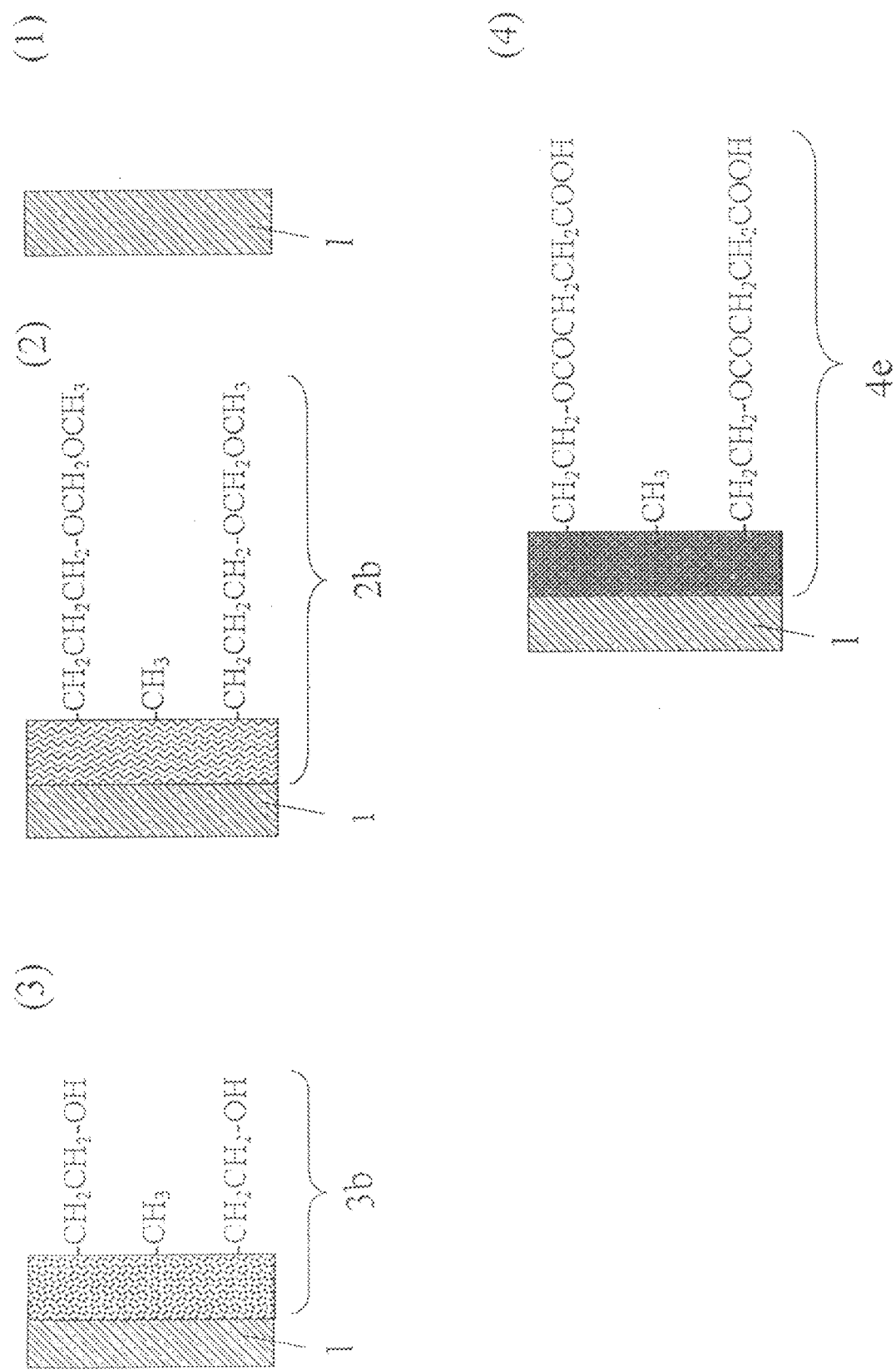
FIG. 5 is a schematic view of a still further embodiment of a method for producing a molecule immobilizing substrate according to the present invention (Example 5)

As shown in FIG. 5(1), a substrate 1 having a silicon oxide film on its surface was immersed into chloroform and then into acetone, followed by ultrasonic cleaning; and then immersed into a piranha solution for 15 minutes, then into water for 1 hour, and further into a toluene solution containing 0.02 mole/L of the 10-(methoxymethoxy)decyltrimethoxysilane obtained in Production Example 1, 0.02 mole/L of octyltrimethoxysilane, and 0.02 mole/L of piperidine for 12 hours, thereby forming, on the substrate, a monomolecular film 2b including methoxymethoxy groups oriented toward an outmost surface of the monomolecular film (FIG. 5(2)). The thus obtained substrate was immersed into chloroform, subsequently into acetone, and then into water, together with ultrasonic cleaning for 5 minutes in each medium. The above treated substrate was immersed into concentrated hydrochloric acid for 12 hours to deprotect the methoxymethoxy groups of the monomolecular film 2b, thereby forming, on the substrate, a monomolecular film 3b including hydroxyl groups oriented toward an outmost surface of the monomolecular film (FIG. 5(3)). Thereafter, the resultant substrate was rinsed by pure water, and then dried in dry air. Next, the resultant substrate was immersed into a pyridine solution containing 1 mole/L of succinic acid anhydride for 12 hours, thereby forming, on the substrate, a monomolecular film 4e including carboxyl groups oriented toward an outmost surface of the monomolecular film (FIG. 5(4)). The resultant substrate was cleaned by water, and then by methanol, followed by drying in dry air.

Comparative Example 1

As shown in FIG. 1(1), a substrate 1 having a silicon oxide film on its surface was immersed into chloroform and then into acetone, followed by ultrasonic cleaning; and then immersed into a piranha solution for 15 minutes, then into water for 1 hour, and further into a toluene solution containing 0.02 mole/L of the 10-(methoxymethoxy)decyltrimethoxysilane obtained in Production Example 1 and 0.02 mole/L of piperidine for 12 hours, thereby forming, on the substrate, a monomolecular film 2a including methoxymethoxy groups oriented toward an outmost surface of the monomolecular film (FIG. 1(2)). The thus obtained substrate was immersed into chloroform, subsequently into acetone, and then into water, together with ultrasonic cleaning for 5 minutes in each medium. The above treated substrate was immersed into concentrated hydrochloric acid for 12 hours to deprotect the methoxymethoxy groups of the monomolecular film 2a, thereby forming, on the substrate, a monomolecular film 3a including hydroxyl groups oriented toward an outmost surface of the monomolecular film (FIG. 1(3)). Thereafter, the resultant substrate was rinsed by pure water, and then dried in dry air.

(Measurement 1)

To confirm the disposition of carboxyl groups at each outmost surface, confirmation of a COO peak was conducted by a surface contact angle with water, and by ESCA (Electron Spectroscopy for Chemical Analysis). The results thereof are listed in Table 1.

Figure 6:
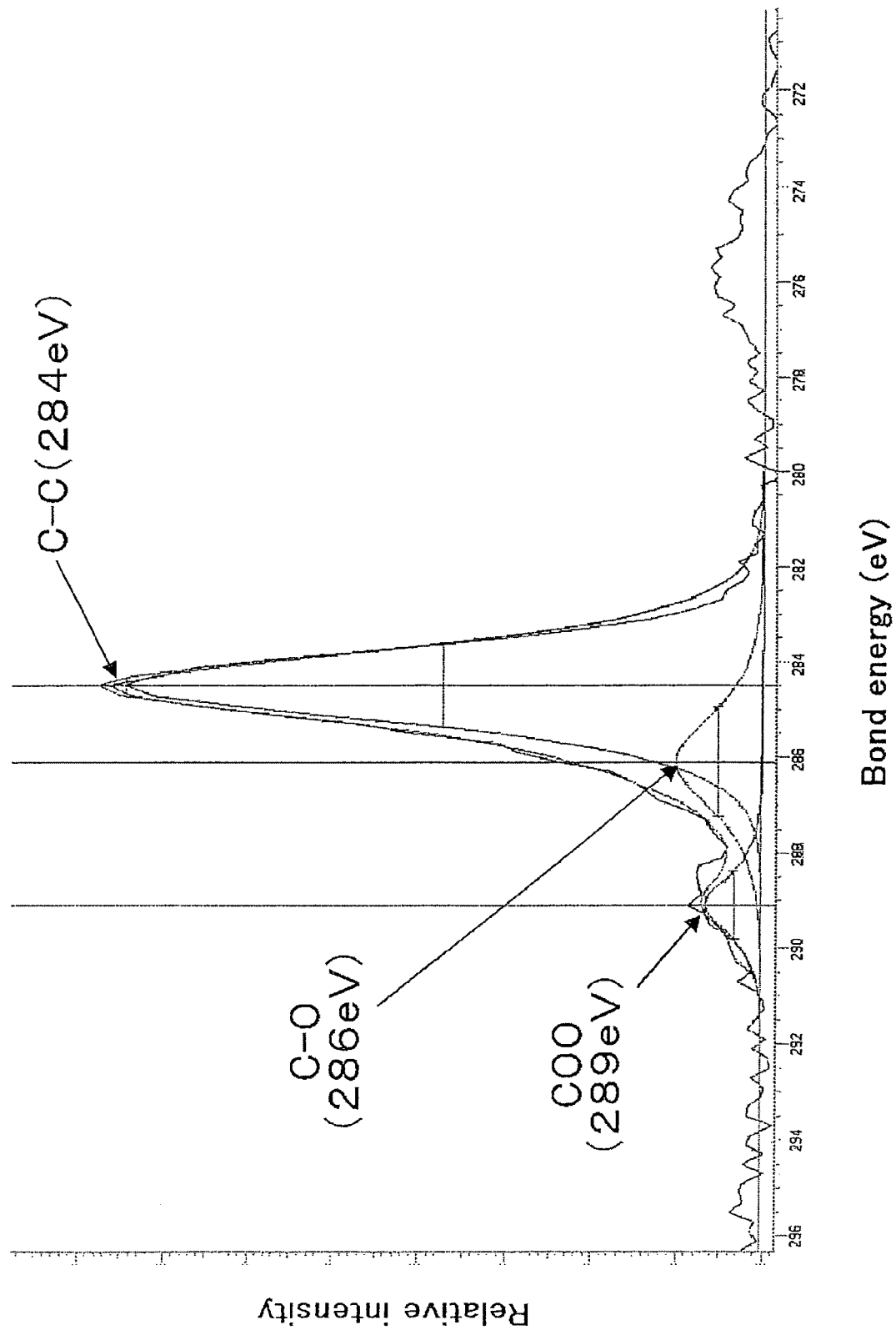
FIG. 6 is an ESCA spectrum showing a COO peak of Example 1.

Further, FIG. 6 shows an ESCA spectrum of Example 1. The ordinate in FIG. 6 represents a relative intensity.

TABLE 1

|  | Surface contact angle | COO peak |
|---|---|---|
| Example 1 | 45° | existence |
| Example 2 | 59° | existence |
| Example 3 | 59° | existence |
| Example 4 | 43° | existence |
| Example 5 | 55° | existence |
| Comparative Example 1 (hydroxyl groups oriented toward an outmost surface of the monomolecular film) | 62° | nonexistence |

To be understood from a variation of surface contact angles in Table 1 is progression of the applicable reactions, and to be understood from confirmation of a COO peak by ESCA is introduction of carboxyl groups onto the applicable substrates.

Namely, it can be said that, since the molecule immobilizing substrates produced by the method of the present invention are formed with the monomolecular films including carboxyl groups oriented toward an outmost surface of the monomolecular films, respectively, molecules of materials for recognition such as proteins which affiliate with carboxyl groups can be immobilized onto the substrates without causing a peeling problem.

Example 6

The substrate obtained in Example 1 was immersed into an N,N-dimethylformamide (DMF) solution containing 0.2M of hydroxy succinic acid imide and 0.2M of diisopropyl-carbodiimide, pulled up therefrom after 12 hours, then successively cleaned by DMF, and then by ethanol, followed by drying in dry air.

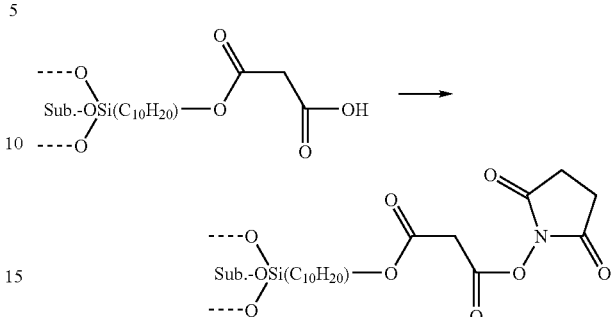

Example 7

The substrate obtained in Example 2 was immersed into a DMF solution containing 0.2M of hydroxy succinic acid imide and 0.2M of diisopropyl-carbodiimide, pulled up therefrom after 12 hours, then successively cleaned by DMF, and then by ethanol, followed by drying in dry air.

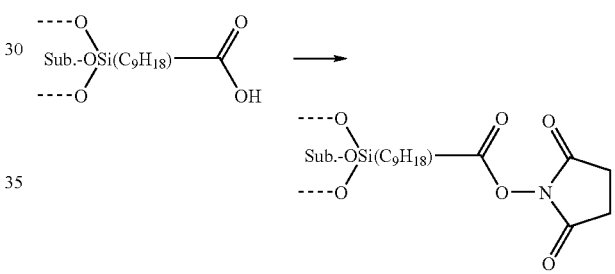

Example 8

The substrate obtained in Example 4 was immersed into a DMF solution containing 0.2M of hydroxy succinic acid imide and 0.2M of diisopropyl-carbodiimide, pulled up therefrom after 12 hours, then successively cleaned by DMF, and then by ethanol, followed by drying in dry air.

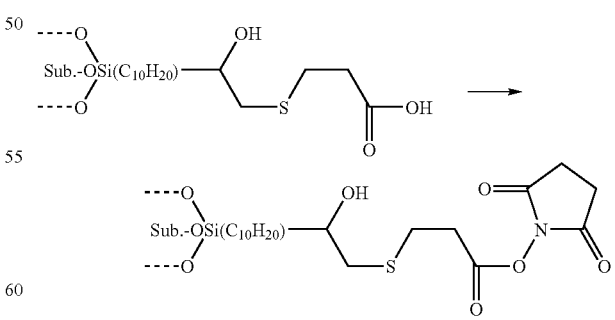

Comparative Example 2

The substrate obtained in Comparative Example 1 was immersed into a DMF solution containing 0.2M of hydroxy succinic acid imide and 0.2M of diisopropyl-carbodiimide, pulled up therefrom after 12 hours, then successively cleaned by DMF, and then by ethanol, followed by drying in dry air.

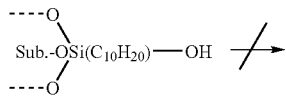

(Measurement 2)

The substrates fabricated in Examples 1, 2, and 4 did not include nitrogen atoms on the monomolecular films located on the substrates, respectively. However, since nitrogen atoms could be introduced onto the monomolecular films by transforming the carboxyl groups located on the surfaces of the substrates into carboxylic acid esters by means of hydroxy succinic acid imide, measurements were conducted by ESCA to each confirm a nitrogen atom peak. Further, surface contact angles with water were measured. The results are listed in Table 2.

Figure 7:
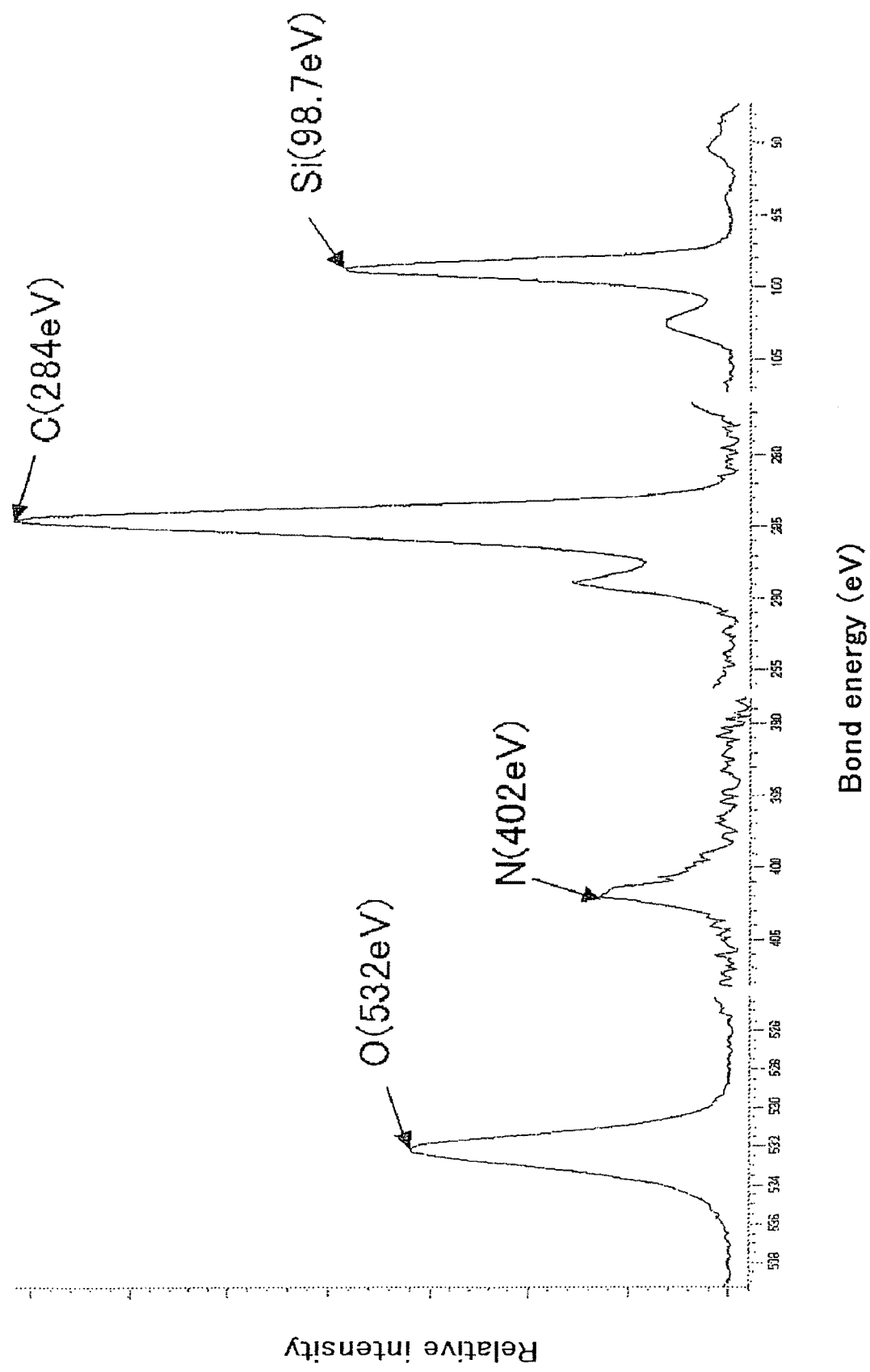
FIG. 7 is an ESCA spectrum showing a nitrogen atom peak of Example 6.

Further, FIG. 7 shows an ESCA spectrum of Example 6. The ordinate in FIG. 7 represents a relative intensity.

TABLE 2

|  | Surface contact angle | Nitrogen atom peak |
| --- | --- | --- |
| Example 6 | 49° | existence |
| Example 7 | 61° | existence |
| Example 8 | 49° | existence |
| Comparative Example 2 | 62° | nonexistence |

To be understood from a variation of surface contact angles in Table 2 is progression of the applicable reactions, and to be understood from confirmation of a nitrogen atom peak by ESCA is introduction of nitrogen atoms onto the applicable substrates.

Namely, it can be said that, since the molecule immobilizing substrates produced by the method of the present invention are formed with the monomolecular films including carboxyl groups oriented toward an outmost surface of the monomolecular films, respectively, it is possible to once esterify the carboxyl groups by means of hydroxysuccinimide or the like, and then to react the esters with amino group ends in amino acids, proteins, or the like to thereby form amides, respectively, such that the intended molecules can be immobilized onto the substrates without causing any peeling problems.

(Measurement 3)

The substrates obtained in Examples 6, 7, 8, and Comparative Example 2 were each immersed into an albumin aqueous solution (1 mg/mL, pH7; the albumin was derived from a calf serum and produced by Sigma Inc.) in an low-temperature chamber (10° C. or below) for about 24 hours, followed by ultrasonic cleaning in pure water, and subjected to measurement by FT-IR (Nicolet 6700, manufactured by Thermo Inc.) ATR method (Examples 9, 10, 11, and Comparative Example 3). Note that the judgment of existence or nonexistence of immobilization of albumin onto each substrate was done based on existence or nonexistence of clear peaks near 1550 and 1670 cm$^{-1}$. The results are listed in Table 3.

TABLE 3

|  | FT-IR peak |
| --- | --- |
| Example 9 | existence |
| Example 10 | existence |
| Example 11 | existence |
| Comparative Example 3 | nonexistence |

By peak confirmation based on FT-IR in Table 3, it is recognized that an albumin is immobilized on each applicable substrate.

Namely, it can be said to have been exemplified that the molecule immobilizing substrate capable of immobilizing thereon molecules without causing a peeling problem can be readily and conveniently produced by the present invention.

The present invention is not limited to the above embodiments. The above embodiments are exemplifications. Any of those which have substantially the same constitution and have the same effects as technical ideas described in claims of the present invention are included in the technical scope of the present invention.

What is claimed is:

1. A method for producing a molecule immobilizing substrate, comprising at least the steps of:
   forming, on a substrate having an oxide and/or hydroxyl group, a monomolecular film including hydroxyl groups, cyano groups, or oxiranyl groups, which are oriented toward an outmost surface of the monomolecular film; and
   chemically modifying the hydroxyl groups, cyano groups, or oxiranyl groups of the monomolecular film to transform them into carboxyl groups, to thereby form, on the substrate, the monomolecular film including the carboxyl groups, which are oriented toward an outmost surface of the monomolecular film,
   wherein
      forming, on the substrate, the monomolecular film including hydroxyl groups, cyano groups, or oxiranyl groups, which are oriented toward an outmost surface of the monomolecular film, comprises
         immersing the substrate in a solution containing silane compounds represented by the following general formulae (2) and (3) mixed with a silane compound represented by general formula (1) having an alkoxymethoxy group including an alkoxyl group moiety having 1 to 6 carbon atoms, cyano group, or oxiranyl group,
      if the silane compound represented by general formula (1) has the alkoxymethoxy group including an alkoxyl group moiety having 1 to 6 carbon atoms as a hydroxyl-group precursory functional group, an acid is reacted with the hydroxyl-group precursory functional group to form, on the substrate, the monomolecular film including the hydroxyl groups, which are oriented toward an outmost surface of the monomolecular film, before chemically modifying the hydroxyl groups, cyano groups, or oxiranyl groups of the monomolecular film, and
      if the silane compound represented by general formula (1) has the oxiranyl group, the oxiranyl group is optionally a hydroxyl-group precursory functional group that is reacted with an acid to form, on the substrate, the monomolecular film including the hydroxyl groups, which are oriented toward an outmost surface of the monomolecular film, before chemically modifying the hydroxyl groups, cyano groups, or oxiranyl groups of the monomolecular film, $$Y_3Si-(CH_2)_m-Z \quad (1)$$

wherein, in formula (1),
"m" represents an integer of 3 to 16;
"Z" represents the alkoxymethoxy group including an alkoxyl group moiety having 1 to 6 carbon atoms, cyano group, or oxiranyl group; and
each "Y" independently represents a halogen atom, or an alkoxyl group having 1 to 4 carbon atoms, and $$Y'_3Si-(CH_2)_n-CH_3 \quad (2)$$

$$Y'_3Si-(CH_2)_n-OCH_3 \quad (3)$$

wherein, in formulae (2) and (3),
"n" represents an integer of 0 to "m";
"m" represents the value in the general formula (1); and
each "Y'" independently represents a halogen atom, or an alkoxyl group having 1 to 4 carbon atoms.

2. The method for producing a molecule immobilizing substrate according to claim 1, wherein chemically modifying the hydroxyl groups to transform them into the carboxyl groups comprises reacting a dicarboxylic anhydride or oxidizing agent with each of the hydroxyl groups.

3. The method for producing a molecule immobilizing substrate according to claim 1, wherein chemically modifying the cyano groups to transform them into the carboxyl groups comprises hydrolyzing the cyano groups.

4. The method for producing a molecule immobilizing substrate according to claim 1, wherein chemically modifying the oxiranyl groups to transform them into the carboxyl groups comprises reacting a thiol having a carboxyl group with each of the oxiranyl groups.

5. The method for producing a molecule immobilizing substrate according to claim 4, wherein reacting the thiol having a carboxyl group with each of the oxiranyl groups comprises conducting addition of a sulfonic acid.

6. The method for producing a molecule immobilizing substrate according to claim 1, wherein in the forming, on the substrate, the monomolecular film including hydroxyl groups, cyano groups, or oxiranyl groups, which are oriented toward an outmost surface of the monomolecular film, by using the silane compound represented by the general formula (1) having the alkoxymethoxy group including an alkoxyl group moiety having 1 to 6 carbon atoms, cyano group, or oxiranyl group, a catalyst comprising an organic base is mixed with the silane compound represented by the general formula (1).

7. The method for producing a molecule immobilizing substrate according to claim 6, wherein the organic base is a pyrrolidine derivative or piperidine derivative.

* * * * *